(12) United States Patent
Esser et al.

(10) Patent No.: US 6,489,330 B1
(45) Date of Patent: Dec. 3, 2002

(54) USE OF PENCICLOVIR FOR THE TREATMENT OF HUMAN HERPES-VIRUS-8

(75) Inventors: Klaus Max Esser, Downingtown, PA (US); Richard Anthony Vere Hodge, Leigh (GB)

(73) Assignee: Novartis International Pharmaceutical Ltd., Hamilton (BM)

( * ) Notice: Subject to any disclaimer, the term of this patent is extended or adjusted under 35 U.S.C. 154(b) by 0 days.

(21) Appl. No.: 09/473,888

(22) Filed: Dec. 29, 1999

Related U.S. Application Data

(63) Continuation of application No. 08/894,929, filed as application No. PCT/EP96/00933 on Mar. 5, 1996.

(30) Foreign Application Priority Data

Mar. 7, 1995 (GB) .............................................. 9504497

(51) Int. Cl.[7] ........................ A61K 31/52; A61K 31/675
(52) U.S. Cl. ..................... 514/261; 514/262; 514/85.4; 514/85.5; 514/85.6; 514/85.7
(58) Field of Search .............................. 424/85.4, 85.5, 424/85.6, 85.7; 514/261, 262

(56) References Cited

FOREIGN PATENT DOCUMENTS

| EP | 0141927 | 5/1985 |
|---|---|---|
| EP | 0182024 | 4/1986 |
| EP | 0216459 | 7/1987 |
| EP | 0 458 363 | 11/1991 |
| WO | WO A 9200742 | 1/1992 |

OTHER PUBLICATIONS

Boyd et al, Antiviral Chemistry & Chemotherapy, vol. 4, supplement 1, pp. 3–11, 1993.*
Clarke et al, 113CA:189452 , 1990.*
Black et al., Medical Virology, vol. 3, "Human Herpesvirus 7," pp. 217–223 (1993).
Clarke et al., Biochimica et Biphysica Acta, 1050, "Epstein-–Barr Virus Gene Expression in Interferon–Treated Cells. Implications for the Regulation of Protein Synmthesis and the Antiviral State," pp. 167–173 (1990).
Feorino et al., Abstract of Poster of the Eighth International Conference on Antiviral Research (ICAR) (1995), "Evaluation of Antiviral Agents Against HHV–6 and HHV–7 in Human Cord Blood Cells".
Feorino et al., Full Poster of the Eighth International Conference on Antiviral Research (ICAR) (1995), "Evaluation of Antiviral Agents Against HHV–6 and HHV–7 in Human Cord Blood Cells".
Nicholas, J., Journal of Virology, vol. 70(9), "Determination and Analysis of the Complete Nucleotide Sequence of Human Herpesvirus 7," pp. 5975–5989 (1996).

Berneman et al., Proc. Natl. Acad. Sci., USA, 89, pp. 10552–10556 (1992).
Frenkel et al., Fields Virology, 3rd. Ed. pp. 20609–20622 (1996).
Harnden et al., vol. 110 Chemical Abstract:173658p, pp. 819 (1989).
Akesson–Johansson et al., Antimicrobial Agents and Chemotherapy, Dec. 1990, vol. 34(12), pp. 2417–2419.
Fields BN et al., Fields Virology, Chapter 15, 3rd Ed, vol. 1, p. 436. (1996).
Liu et al., Antiviral Chemistry & Chemotherapy (1990), 1(5), pp. 313–318.
Agut et al., Institut Pasteur/Elsevier, (1989), 140(3) pp. 219–228.
Harnden et al., J. Chem. Soc, Perkin Trans. I, (1988) 10, pp. 2777–2784.
Ablashi D. V. et al. In Vivo, vol. 5 (3), 1991, pp. 193–200.
Fields B N et al., Fields Virology, Chapter 71, p. 2221 (1996).
J.B. Black et al., Virus Research 52 (1997) pp. 25–41.
Vere Hodge RA. et al., Antiviral Chemistry and Chemotherapy (1993) 4 Suppl. 1, pp. 13–24.
Earnshaw D.L. et al., Antimicrobial Agents and Chemotherapy (1992) 36, pp. 2747–2757.
Vere Hodge et al., Antimicrobial Agents and Chemotherapy (1989) 33, pp. 223–229.
Boyd et al., Antimicrobial Agents and Chemotherapy (1987) 31, pp. 1238–1242.
Larsson A. et al., Antimicrobial Agents and Chemotherapy (1986) 30. pp. 598–605.
Boyd et al., Antiviral Chem. Chemother, Suppl., 4(1), pp. 3–11 (1993).
Luppi et al., Haematologica, 81(3), pp. 265–281 (1996).
Fields et al., Fields Virology, 3rd Ed., Phila.-NY, p. 2595 (1995).

\* cited by examiner

*Primary Examiner*—Russell Travers
(74) *Attorney, Agent, or Firm*—Thomas R. Savitsky

(57) ABSTRACT

The present invention is directed to the use of a compound of Formula (A),

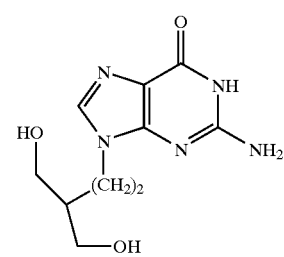

or a bioprecursor, or a pharmaceutically acceptable salt, phosphate ester and/or acyl derivative of either of the foregoing in the manufacture of a medicament for use in the treatment, including prophylaxis of HHV-8 infection.

22 Claims, No Drawings

USE OF PENCICLOVIR FOR THE TREATMENT OF HUMAN HERPES-VIRUS-8

This application is a continuation of U.S. Ser. No. 08/894,929, filed Feb. 24, 1998, which is the §371 national stage entry of PCT/EP96/00933, filed Mar. 5, 1996.

This invention relates to treatment of medical conditions associated with infection with human herpesvirus 8 (HHV-8), and to the use of compounds in the preparation of a medicament for use in the treatment of such conditions.

When used herein, 'treatment' includes prophylaxis as appropriate.

EP-A-141927 (Beecham Group p.l.c.) discloses penciclovir, the compound of formula (A):

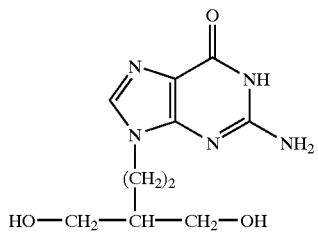

and salts, phosphate esters and acyl derivatives thereof, as antiviral agents. The sodium salt hydrate of penciclovir is disclosed in EP-A-216459 (Beecham Group p.l.c.). Penciclovir and its antiviral activity is also disclosed in Abstract P.V11-5 p.193 of 'Abstacts of 14th Int. Congress of Microbiology', Manchester, England Sep. 7–13, 1986 Boyd et. al.).

Orally active bioprecursors of the compound of formula (A) are of formula (B):

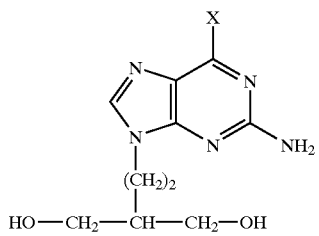

and salts and derivatives thereof as defined under formula (A): wherein X is $C_{1-6}$ alkoxy, $NH_2$ or hydrogen. The compounds of formula (B) wherein X is $C_{1-6}$ alkoxy or $NH_2$ are disclosed in EP-A-141927 and the compounds of formula (B) wherein X is hydrogen, disclosed in EP-A-182024 (Beecham Group p.l.c.) are preferred prodrugs. A particularly preferred example of a compound of formula (B) is that wherein X is hydrogen and wherein the two OH groups are in the form of the acetyl derivative, described in Example 2 of EP-A-182024, hereinafter referred to as famciclovir.

The compounds of formulae (A) and (B) and salts and derivatives thereof have been described as potentially effective in the treatment of infections caused by herpesviruses, such as herpes simplex type 1, herpes simplex type 2, varicella-zoster, Epstein-Barr viruses, and cytomegalovirus. Famciclovir, sold in the United Kingdom and the United States of America under the trademark, FAMVIR, is used for treating herpes zoster (shingles).

Human herpesvirus 8 (HHV-8) is a recently discovered member of the family Herpesviridae. The virus is first reported by Chang et al in 'Science' Vol 266, Dec. 16th, 1994, p1865 and termed HHV-8 by Schulz et al in 'Nature' Vol 373, Jan. 5th, 1995, p17. This virus is described therein as being associated with Kaposi's Sarcoma (KS), the most common neoplasm ocurring in persons with aquired immunodeficiency syndrome (AIDS). Agents previously suspected of causing KS include cytomegalovirus (CMV), hepatitis B virus, human herpesvirus 6, HIV and *Mycoplasma penetrans*. It is possible that HHV-8 is associated with other proliferative diseases, involving various cell types, including endothelial, epithelial, neuronal, pancreatic, myeloid cell types, and inflammatory, autoimmune-like, and tissue degenerative diseases such as rheumatoid arthritis, lupus eritematosis and multiple sclerosis. It is also possible that HHV-8 is associated with AIDS related illness. When used herein, the alternative term for HHV-8, which is 'Kaposis Sarcoma-associated Herpes Virus', is included.

It has now been discovered that the above compounds have potential activity against HHV-8.

Accordingly, the present invention provides a method of treatment of HHV-8 infection in humans, which method comprises the administration to the human in need of such treatment, an effective amount of a compound of formula (A):

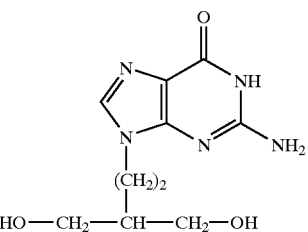

or a bioprecursor, or a pharmaceutically acceptable salt, phosphate ester and/or acyl derivative of either of the foregoing.

The term 'acyl derivative' is used herein to include any derivative of the compounds of formula (A) in which one or more acyl groups are present. Such derivatives are included as bioprecursors of the compounds of formula (A) in addition to those derivatives which are per se biologically active.

The compound of formula (A) may be in one of the forms disclosed in EP-A-216459 (Beecham Group p.l.c.).

Examples of bioprecursors, pharmaceutically acceptable salts and derivatives are as described in the aforementioned European Patent references, the subject matter of which are incorporated herein by reference.

A particular compound of formula (B) of interest is 9-(4-acetoxy-3-accroxymethylbut-1-yl)-2-aminopurine, known as famciclovir (FCV), the well-absorbed oral form of penciclovir (PCV).

The compound of formula (A), bioprecursors, salts and derivatives may be prepared as described in the aforementioned European Patent references.

The compound, in particular, famciclovir, may be administered by the oral route to humans and may be compounded in the form of syrup, tablets or capsule. When in the form of a tablet, any pharmaceutical carrier suitable for formulating such solid compositions may be used, for example magnesium stearate, starch, lactose, glucose, rice, flour and chalk. The compound may also be in the form of an ingestible capsule, for example of gelatin, to contain the compound, or in the form of a syrup, a solution or a suspension. Suitable liquid pharmaceutical carriers include ethyl alcohol, glycerine, saline and water to which flavouring or colouring agents may be added to form syrups.

For parenteral administration, fluid unit dose forms are prepared containing the compound and a sterile vehicle. The compound depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention.

Preferred parenteral formulations include aqueous formulations using sterile water or normal saline, at a pH of around 7.4 or greater, in particular, containing penciclovir sodium salt hydrate.

As is common practice, the compositions will usually be accompanied by written or printed directions for use in the medical treatment concerned.

An amount effective to treat the virus infection depends on the nature and severity of the infection and the weight of the mammal.

A suitable dosage unit might contain from 50 mg to 5 g of active ingredient, such as 100 g to 2 g, for example 100 to 500 or 1500 mg. Such doses may be administered 1 to 4 times a day or more usually 2 or 3 times a day. The effective dose of compound will, in general, be in the range of from 0.2 to 40 mg per kilogram of body weight per day or, more usually, 10 to 20 mg/kg per day. In the case of famciclovir, the dosage unit may be 125 mg, 250 mg, 500 mg, 750 mg, 1000 mg, 1250 mg or 1500 mg.

Penciclovir may also be administered topically, in a suitable formulation, for example as a cream.

The present invention also provides the use of a compound of formula (A) or a bioprecursor, or a pharmaceutically acceptable salt, phosphate ester and/or acyl derivative of either of the foregoing, in the preparation of a medicament for use in the treatment of HHV-8 infection. Such treatment may be carried out in the manner as hereinbefore described.

The present invention further provides a pharmaceutical composition for use in the treatment of HHV-8 infection, which comprises an effective amount of a compound of formula (A) or a bioprecursor, or a pharmaceutically acceptable salt, phosphate ester and/or acyl derivative of either of the foregoing, and a pharmaceutically acceptable carrier. Such compositions may be prepared in the manner as hereinafter described.

The compound of formula (A) and its prodrugs show a synergistic antiviral effect in conjunction with interferons; and treatment using combination products comprising these two components for sequential or concomitant administration, by the same or different routes, are therefore within the ambit of the present invention. Such products are described in EP-A-271270 (Beecham Group p.l.c.). Combinations with other immunomodulatory compounds, such as other cytolines or cytokine inducers, or other compounds that stimulate or suppress the immune response are also within the ambit of this invention.

What is claimed is:

1. A method for the treatment of HHV-8 infection in mammals, including humans, which method comprises administering to the mammal in need of such treatment, an effective amount of a compound of formula (A):

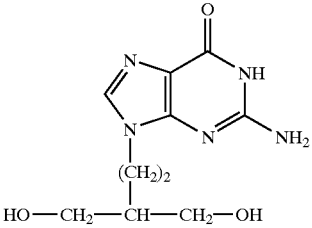

or a bioprecursor, or a pharmaceutically acceptable salt, phosphate ester and/or acyl derivative of either of the foregoing.

2. The method according to claim 1 wherein the treatment is for Kaposi's Sarcoma.

3. The method according to claim 1 wherein the treatment is for AIDS related illness.

4. The method according to claim 1 wherein the compound is famciclovir.

5. The method according to claim 4 wherein famciclovir is administered at a dose of 125 mg, 250 mg, 500 mg, 750 mg, 1000 mg, 1250 mg or 1500 mg once daily.

6. The method according to claim 4 wherein famciclovir is administered at a dose of 125 mg, 250 mg, 500 mg, 750 mg, 1000 mg, 1250 mg or 1500 mg twice daily.

7. The method according to claim 4 wherein famciclovir is administered at a dose of 125 mg, 250 mg, 500 mg, 750 mg, 1000 mg, 1250 mg or 1500 mg three times daily.

8. The method according to claim 1 wherein the compound of Formula (I), or a bioprecurser, or a pharmaceutically acceptable salt, phosphate ester and/or acyl derivative of either of the foregoing, is administered in combination with an immunomodulatory agent.

9. The method according to claim 8 wherein the immunomodulatory agent is interferon.

10. A method for the treatment of HHV-8 infection in a mammal, which method comprises administering to a mammal in need thereof, an effective amount of the compound penciclovir.

11. The method according to claim 10 wherein the compound is administered in combination with an immunomodulatory agent.

12. The method according to claim 11 wherein the immunomodulatory agent is interferon.

13. A method for prophylactic treatment of an HHV-8 infection in a mammal in needed thereof which method comprises administering to said mammal an effective amount of the compound penciclovir.

14. The method according to claim 13 wherein the compound is administered in combination with an immunomodulatory agent.

15. The method according to claim 14 wherein the immunomodulatory agent is interferon.

16. The method according to claim 4 wherein the compound is administered in combination with an immunomodulatory agent.

17. The method according to claim 16 wherein the immunomodulatory agent is interferon.

18. A method for the prophylactic treatment of an HHV-8 infection in a mammal in needed thereof which method comprises administering to said mammal an effective amount of a compound of Formula (A):

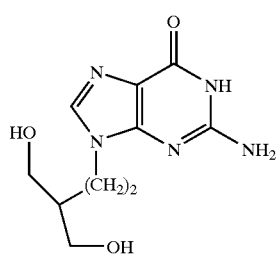

or a bioprecurser, or a pharmaceutically acceptable salt, phosphate ester and/or acyl derivative of either of the foregoing.

19. The method according to claim 18 wherein the prophylactic treatment is for Kaposi's Sarcoma.

20. The method according to claim 18 wherein the prophylactic treatment is for AIDS related illness.

21. The method according to claim 18 wherein the compound is administered in combination with an immunomodulatory agent.

22. The method according to claim 21 wherein the immunomodulatory agent is interferon.

* * * * *